US012453867B2

(12) United States Patent
Kuusela

(10) Patent No.: US 12,453,867 B2
(45) Date of Patent: Oct. 28, 2025

(54) RADIATION TREATMENT PLAN OPTIMIZATION METHOD AND APPARATUS

(71) Applicant: Siemens Healthineers International AG, Steinhausen (CH)

(72) Inventor: Esa Kuusela, Espoo (FI)

(73) Assignee: Siemens Healthineers International AG, Steinhausen (CH)

( * ) Notice: Subject to any disclaimer, the term of this patent is extended or adjusted under 35 U.S.C. 154(b) by 247 days.

(21) Appl. No.: 18/203,902

(22) Filed: May 31, 2023

(65) Prior Publication Data

US 2024/0399169 A1 Dec. 5, 2024

(51) Int. Cl.
*A61N 5/10* (2006.01)

(52) U.S. Cl.
CPC .................................. *A61N 5/1031* (2013.01)

(58) Field of Classification Search
CPC ...... A61N 5/1031; A61N 5/103; G16H 30/20; G16H 40/63; G16H 40/67; G16H 50/20; G16H 20/40
See application file for complete search history.

(56) References Cited

U.S. PATENT DOCUMENTS

2019/0046813 A1* 2/2019 Zhou ........................ H04L 67/01
2022/0168592 A1 6/2022 Neukirchen

FOREIGN PATENT DOCUMENTS

CN 109785931 A 5/2019

OTHER PUBLICATIONS

Chow, James C.L.; Internet-based computer technology on radiotherapy; Reports of Practical Oncology and Radiotherapy, vol. 22, No. 6; Sep. 8, 2017, pp. 455-462; DOI: 10.1016/J.RPOR.2017.08.005.

PCT International Search Report and Written Opinion from related Application No. PCT/EP2024/064847, dated Aug. 9, 2024; 17 pages.

* cited by examiner

*Primary Examiner* — Kiho Kim
(74) *Attorney, Agent, or Firm* — Fitch, Even, Tabin & Flannery LLP

(57) ABSTRACT

A control circuit, while optimizing a radiation treatment plan for a particular patient, outsources an optimization calculation to an external resource and then receives from that external resource a resultant optimization calculation. By one approach, that optimization calculation comprises an optimization high-level utility function calculation. The external resource may comprise, for example, a third-party resource.

20 Claims, 4 Drawing Sheets

RADIATION TREATMENT PLAN OPTIMIZATION METHOD AND APPARATUS

TECHNICAL FIELD

These teachings relate generally to treating a patient's planning target volume with energy pursuant to an energy-based treatment plan and more particularly to optimizing an energy-based treatment plan.

BACKGROUND

The use of energy to treat medical conditions comprises a known area of prior art endeavor. For example, radiation therapy comprises an important component of many treatment plans for reducing or eliminating unwanted tumors. Unfortunately, applied energy does not inherently discriminate between unwanted material and adjacent tissues, organs, or the like that are desired or even critical to continued survival of the patient. As a result, energy such as radiation is ordinarily applied in a carefully administered manner to at least attempt to restrict the energy to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often automatically generated through a so-called optimization process. As used herein, "optimization" will be understood to refer to improving a candidate treatment plan without necessarily ensuring that the optimized result is, in fact, the singular best solution. Such optimization often includes automatically adjusting one or more physical treatment parameters (often while observing one or more corresponding limits in these regards) and mathematically calculating a likely corresponding treatment result (such as a level of dosing) to identify a given set of treatment parameters that represent a good compromise between the desired therapeutic result and avoidance of undesired collateral effects.

Typically, high-level utility functions (HLUF's) in radiation treatment planning optimization do not adhere to or reflect a well-defined universally-agreed format. That said, the applicant has determined that using different functional forms can potentially lead to very different optimization behaviors. As things stand, typical current radiation treatment plan optimizers do not support free utility function definitions.

BRIEF DESCRIPTION OF THE DRAWINGS

The above needs are at least partially met through provision of the radiation treatment plan optimization method and apparatus described in the following detailed description, particularly when studied in conjunction with the drawings, wherein.

Figure 1:
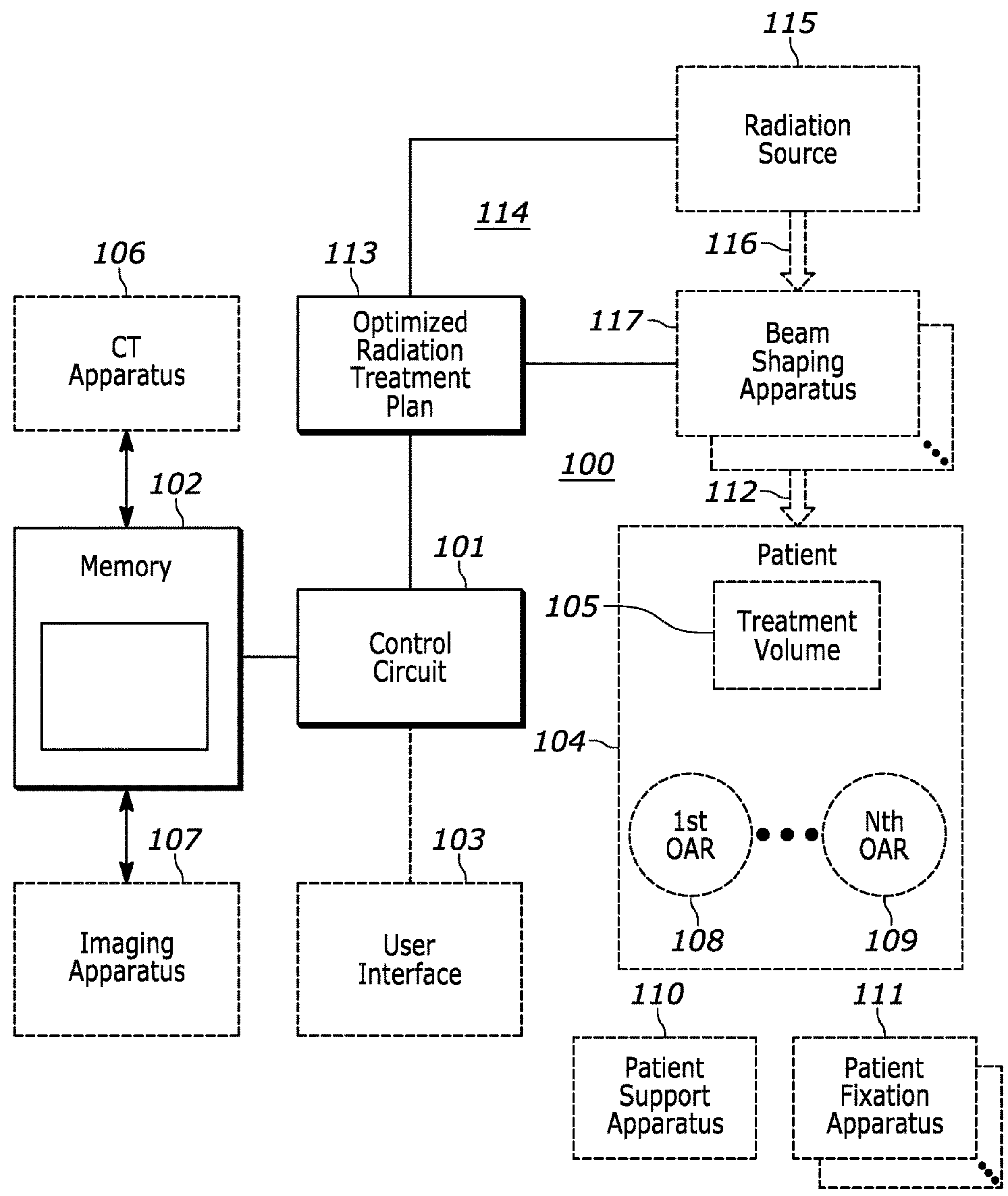
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, pursuant to these various embodiments, a control circuit, while optimizing a radiation treatment plan for a particular patient, outsources an optimization calculation to an external resource and then receives from that external resource a resultant optimization calculation. By one approach, that optimization calculation comprises an optimization high-level utility function calculation. The external resource may comprise, for example, a third-party resource.

By one approach, that optimization calculation comprises an optimization cost function. By one approach, the control circuit cannot control a formatting of a function by which the external resource calculates the optimization calculation.

By one approach, the control circuit is configured to outsource the optimization calculation to the external resource once (and only once) during each optimization loop. By another approach, the control circuit is configured to outsource an optimization calculation to the external resource (or resources) more than once during each optimization loop.

These teachings are highly flexible in practice. For example, by one approach the control circuit is further configured to determine at least one (or two, or three or more) optimization variable values and to then provide those optimization variable values to the external resource when outsourcing the optimization calculation. As another example, the control circuit can be further configured to receive an address for the external resource and to then use that received address when outsourcing the optimization calculation to the external resource.

So configured, while typical current approaches enforce a certain functional form and hence inherent limitations with respect to how much the functional form can be tuned, the present teachings provide the user with the ability to freely define the functional form of the high-level utility function.

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as optimization information for a particular patient and information regarding a particular radiation treatment platform as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

By one approach, a computed tomography apparatus 106 and/or other imaging apparatus 107 as are known in the art can source some or all of any desired patient-related imaging information.

In this illustrative example the control circuit 101 is configured to ultimately output an optimized energy-based treatment plan (such as, for example, an optimized radiation treatment plan 113). This energy-based treatment plan typically comprises specified values for each of a variety of treatment-platform parameters during each of a plurality of sequential exposure fields. In this case the energy-based treatment plan is generated through an optimization process, examples of which are provided further herein.

By one approach the control circuit 101 can operably couple to an energy-based treatment platform 114 that is configured to deliver therapeutic energy 112 to a corresponding patient 104 having at least one treatment volume 105 and also one or more organs-at-risk (represented in FIG. 1 by a first through an Nth organ-at-risk 108 and 109) in accordance with the optimized energy-based treatment plan 113. These teachings are generally applicable for use with any of a wide variety of energy-based treatment platforms/apparatuses. In a typical application setting the energy-based treatment platform 114 will include an energy source such as a radiation source 115 of ionizing radiation 116.

By one approach this radiation source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the radiation source 115 along that arcuate pathway, and may accordingly control when the radiation source 115 starts moving, stops moving, accelerates, de-accelerates, and/or a velocity at which the radiation source 115 travels along the arcuate pathway.

As one illustrative example, the radiation source 115 can comprise, for example, a radio-frequency (RF) linear particle accelerator-based (linac-based) x-ray source. A linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical energy-based treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more energy-shaping apparatuses (for example, beam-shaping apparatuses 117 such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction) during an energy-based treatment session by the control circuit 101. As the foregoing elements and systems are well understood in the art, further elaboration in these regards is not provided here except where otherwise relevant to the description.

Figure 2:
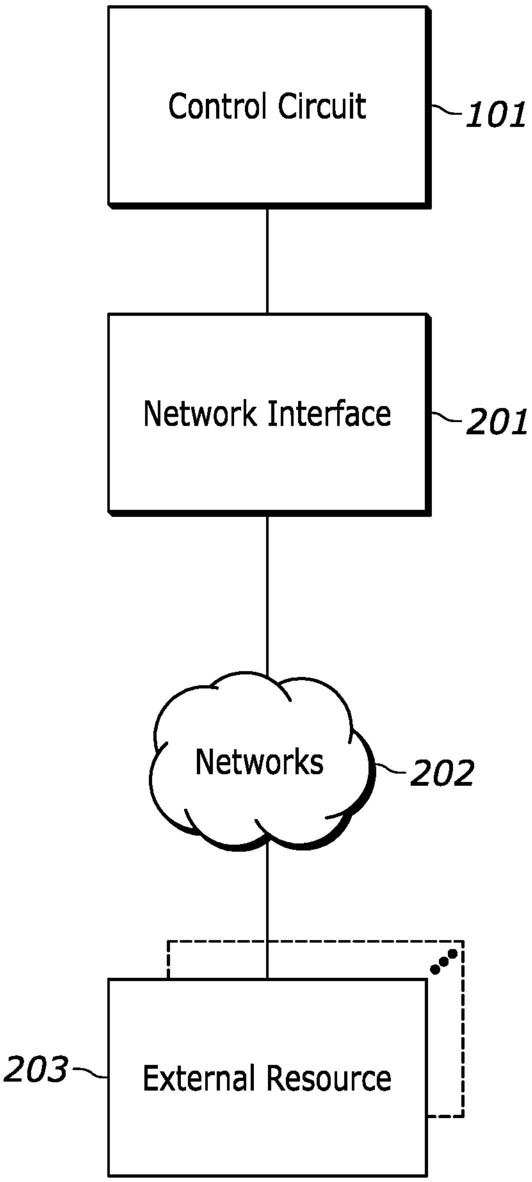
FIG. 2 comprises a block diagram as configured in accordance with various embodiments of these teachings.

Referring now to FIG. 2, the aforementioned control circuit 101 can also couple to a network interface 201. Numerous examples of network interfaces are known in the art. A non-exhaustive listing would include Universal Serial Bus (USB)-based interfaces, RS232-based interfaces, I.E.E.E. 1394 (aka Firewire)-based interfaces, Ethernet-based interfaces, any of a variety of so-called Wi-Fi™-based wireless interfaces, Bluetooth™-based wireless interfaces, cellular telephony-based wireless interfaces, Near Field Communications (NFC)-based wireless interfaces, standard telephone landline-based interfaces, cable modem-based interfaces, and digital subscriber line (DSL)-based interfaces.

The network interface 201 can be selectively employed to communicatively couple the control circuit 101, via one or more intervening networks 202 (such as, but not limited to, the Internet), to one or more external resources 203. An external resource 203 may comprise, for example, a server configured to interact with network entities such as the control circuit 101 as described herein. By one approach, the external resource 203 comprises a third-party resource, which is to say, the external resource 203 is maintained and operated by an entity other than the entity that controls the control circuit 101.

Figure 3:
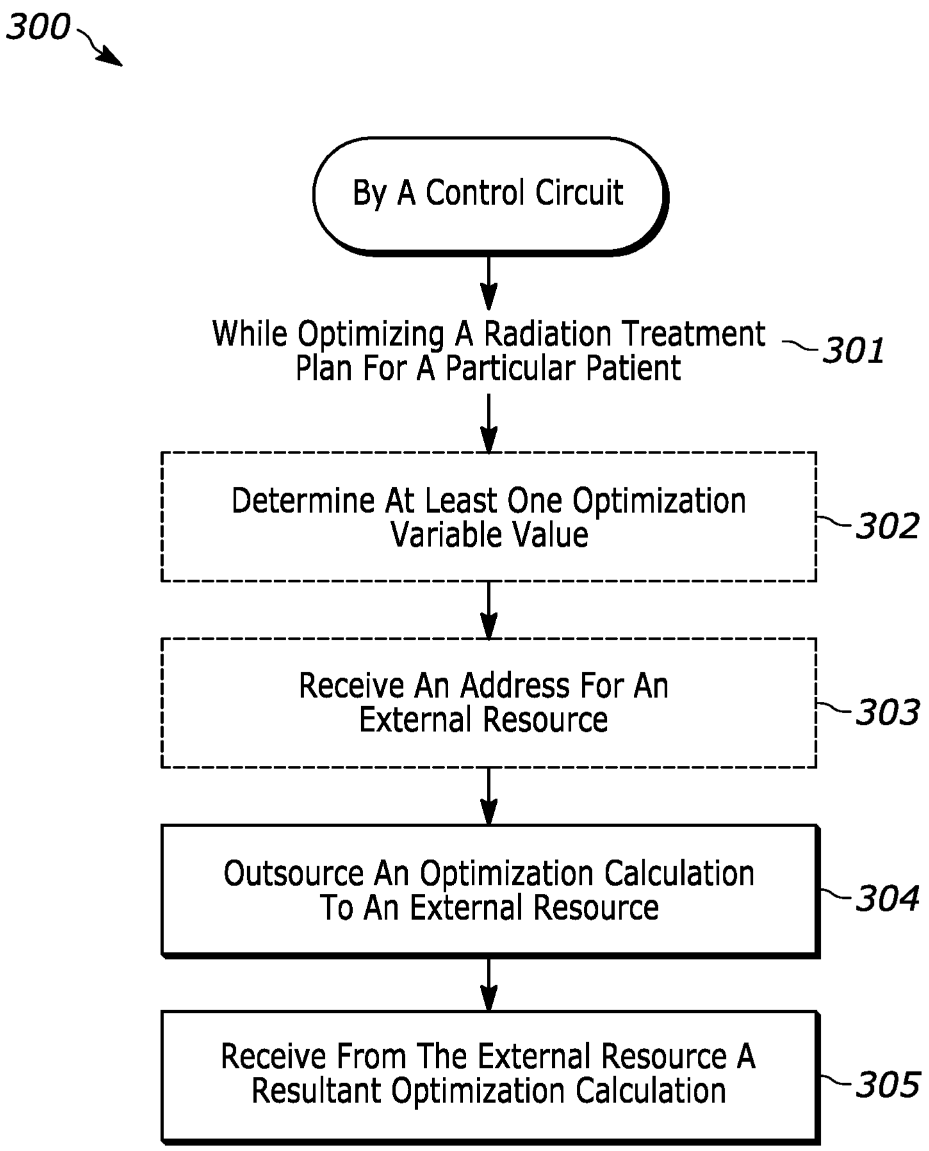
FIG. 3 comprises a flow diagram as configured in accordance with various embodiments of these teachings.

Referring now to FIG. 3, a process 300 that can be carried out, for example, in conjunction with the above-described application setting (and more particularly via the aforementioned control circuit 101) will be described. Generally speaking, this process 300 serves to facilitate generating an optimized radiation treatment plan 113 to thereby facilitate treating a particular patient with therapeutic radiation using a particular radiation treatment platform per that optimized radiation treatment plan. More particularly, this process 300 is carried out while the control circuit 101 is optimizing a radiation treatment plan for a particular patient (as denoted by reference numeral 301).

At optional block 302, by one approach this process 300 can provide for the control circuit 101 being configured to determine at least one optimization variable value. If desired, this activity can comprise determining at least two different optimization variable values. By yet another approach, this activity can comprise determining at least three different optimization variable values, or more as desired. Illustrative examples in these regards are provided below.

By one approach, the control circuit 101 may be pre-provisioned with an address for an external resource 203. By another approach, and as provided at optional block 303, the control circuit 101 can receive an address for an external resource at a time of need (for example, during the optimization process). By one approach, the control circuit 101 may have access to a plurality of addresses for a corresponding plurality of external resources 303. In such a case, the control circuit 101 may select a particular external resource 303 for use during the optimization process as a function of corresponding selection criteria. The latter will accommodate, if desired, selecting different external resources 303 for use during different optimization cycles (and/or during different parts of a single optimization cycle) that collectively serve the optimization process.

At block 304, the control circuit 101 outsources at least one optimization calculation to an external resource 203 (such as, for example, an external resource 203 that corresponds to the aforementioned received address). In the case where the control circuit 101 previously determined one or more optimization variable values, the control circuit 101 can include those values when outsourcing this optimization calculation (or calculations). These teachings are flexible in practice and will accommodate various approaches in these regards. By one approach, for example, the outsourced optimization calculation may comprise an optimization cost function.

By one approach, the outsourced optimization calculation comprises an optimization high-level utility function calculation. In this example, it is presumed that the high-level utility function is a function that can evaluate any combination of a set of candidate degrees-of-freedoms (such as fluence maps and/or machine control points) and resolve that evaluation into a single representative number. The optimization process can then find the particular set of degrees-of-freedom that maximize the utility (or minimize the cost) (or that at least finds a solution that is close enough to the true minimum cost to be acceptable). By one approach, the high-level utility function can describe how a clinician might evaluate different combinations of obtained metric values.

Those skilled in the art will understand that a high-level utility function can be expressed using any of a variety of formats. By one approach, control circuit 101 is configured such that the control circuit 101 cannot control the formatting of the function by which the external resource 203 calculates the optimization calculation. As one example, the format of the high-level utility function could be a weighted sum of different terms, with each term being calculated based on the provided information. As an example of a term, these teachings would readily accommodate any mathematical formula used in tumor control probability (TCP) and normal tissue complications probability (NTCP) models, or the scoring function in plan quality evaluation scorecards. As another example, the functional form could comprise a non-linear combination (having, for example, multiple multiplicative terms) or even a neural network. As yet another example, the format could comprise an algorithmic presentation that lacks any explicit format.

So configured, the shape of the high-level utility function can be set to accord to the preferences of, for example, a research-oriented customer seeking to study or define such a capability.

At block 305, a control circuit 101 receives from the aforementioned external resource 203 a resultant optimization calculation (calculated, for example, using optimization variable values that the control circuit 101 may have provided to the external resource 203). That received result (or results) can then be used during the current optimization cycle by the control circuit 101 in ordinary course to facilitate optimizing a resultant radiation treatment plan for the particular patient.

When optimization concludes, the resultant optimized radiation treatment plan 113 can then be used to administer therapeutic radiation to the particular patient via, for example, the aforementioned radiation treatment platform 114.

Figure 4:
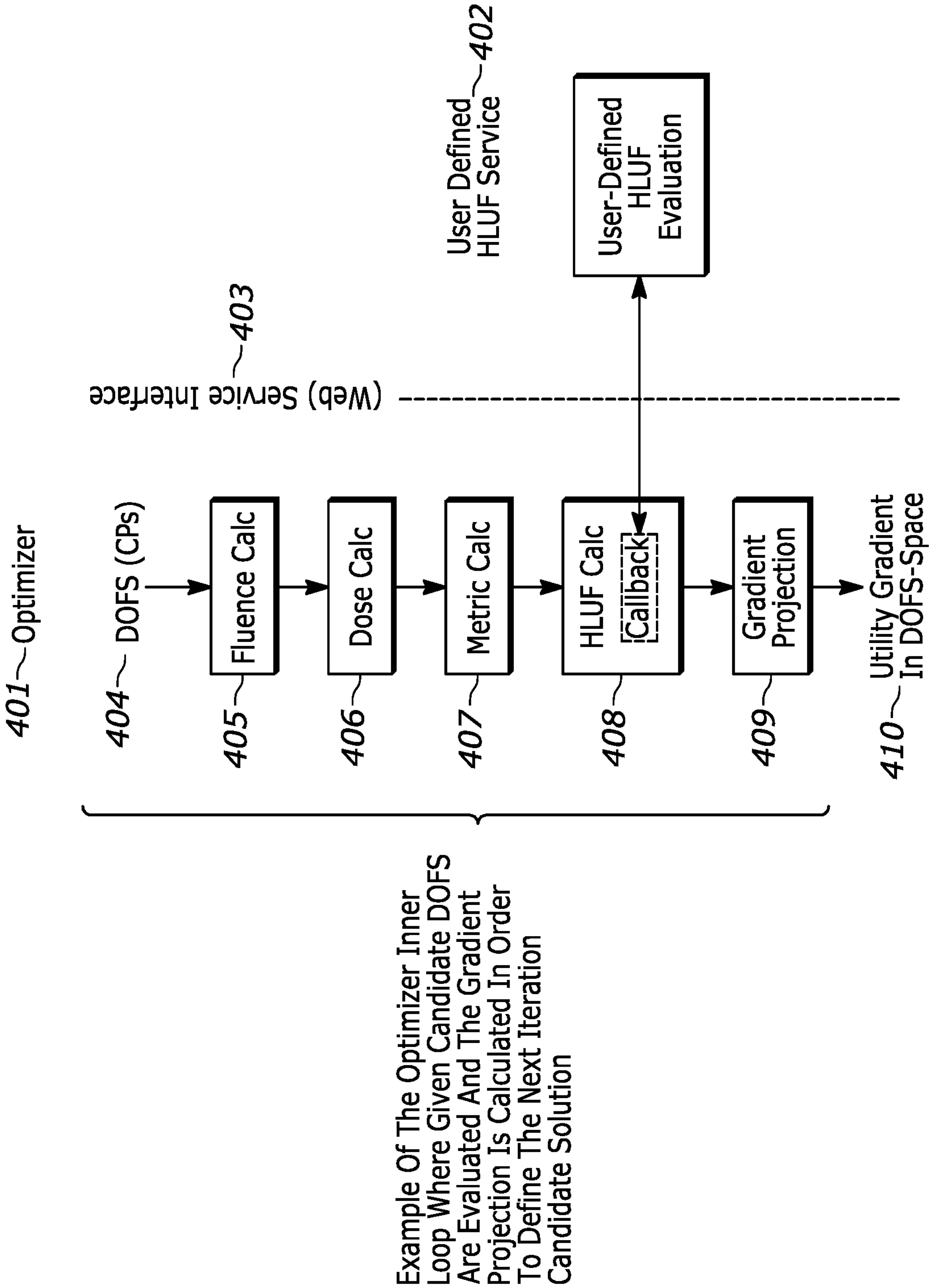
FIG. 4 comprises a block diagram as configured in accordance with various embodiments of these teachings.

Referring now to FIG. 4, the details of a particular instantiation of these teachings will be provided. It will be understood that the details of this example are intended only to provide an illustrative example and are not intended to suggest any limitations with respect to these teachings.

This example presents an optimizer 401 that interacts by way of a web-based service interface 403 with an external resource that provides a user-defined high-level utility function service 402. FIG. 4 illustrates some steps taken within an optimizer inner loop to evaluate candidate degrees-of-freedom and a resultant gradient projection is calculated to thereby aid in defining a next iteration candidate solution for a radiation treatment plan.

Given a set of candidate degrees-of-freedom (as denoted by reference numeral 404 and pertaining, in this example, to a plurality of control points as is well understood in the art), the optimizer 401 calculates a corresponding fluence (at block 405), a corresponding dose (at block 406), and at least one corresponding metric (at block 407). A non-exhaustive listing of useful metrics might include the mean dose of organ-at-risk, (or gEUD—Generalized Equivalent Uniform Dose) and metrics related to dose distribution or organs or targets (such as, but not limited to, Dose-to-Volume, Volume-to-dose, max-dose, target coverage, dose homogeneity index, max dose at a certain distance from the target, dose conformality index, and volume of regret). These teachings will also accommodate metrics that are related to leaf sequences or fluence (such as, but not limited to, total monitor units, total treatment time, fluence smoothness related metrics (for example, total change in neighboring fluence pixels), and aperture shape related metrics (for example, total multiple-leaf collimator aperture boundary length).

At block 408 the optimizer 401 then transmits those values to the high-level user function 302 which evaluates that data per the particular format/approach that is supported by the user defined high-level utility function service 302 and then returns a corresponding resultant gradient projection that leads to a utility gradient in degrees-of-freedom space 410. (The word "callback" is used in this illustration in a loose sense to describe that in lieu of calling a high-level utility function as part of the native optimization algorithm code, the high-level utility function evaluation is instead handled by calling a separate service that serves this purpose.)

With continued reference to the foregoing example, any cost function, which can, if desired, be converted to a corresponding utility function by multiplying the former with a negative number), can be defined as $$U(F) = \tilde{U}(M(F))$$

where vector F represents the degrees-of-freedom (for example, fluence maps or machine control points), and M(F) represents the function that maps the degrees-of-freedom into corresponding metric values. (In practice this could, for example, include a first fluence calculation from the control points, followed by a corresponding dose evaluation, and then a dose-volume-histogram (DVH) calculation based on the calculated dose in the region belonging to a certain critical organ, and finally evaluating a certain location in the DVH). $\tilde{U}(M)$, in turn, represents the high-level utility function that is essentially just a function of vectors of metric values and yields a single number that describes the clinical value of the current metric values (in turn reflecting how the current candidate degrees-of-freedom are performing along these metrics).

It will be appreciated that in the above-described approach, the numerically challenging part of a single optimization loop is likely the metric calculation. The performance of the high-level utility function is seldom a significant contributor to the total optimization time since the dimensionality of the metric vector could be three or four orders of magnitude smaller than the dimensionality of the degrees-of-freedom.

By one approach, the user defined high-level utility function can be evaluated by launching a predefined service for the evaluation as described herein. This service can respond to a request (which request includes or otherwise refers to current metric values as input) with cost and/or gradient information as output. In such a case, upon launching an optimization task, the high-level utility function parametrization need not be given as input. Instead, the user can provide an address for this high-level utility function evaluation service. As one example in these regards, the high-level utility function calculation can be provided via a Restful-API web socket and the user can provide the port number for the algorithm to utilize to access the service.

Those skilled in the art will recognize that a wide variety of modifications, alterations, and combinations can be made with respect to the above-described embodiments without departing from the scope of these teachings. For example, these teachings will accommodate several ways to organize accessing the high-level utility function. One possibility is that the high-level utility function service is run in a separate process that is separately launched. And there exist multiple technical possibilities to organize the communication between the optimization process and the high-level utility function calculation service. By another approach, a research-oriented user could prefer to launch the optimization service in some development environment in the same process and providing the high-level utility function calculator as a function pointer. Note that it is also possible to organize the high-level utility function service so that there are separate calls for calculating cost, gradient, or higher derivates. By yet another approach, there could be calls that provide as output certain combinations of the foregoing (to, for example, efficiently support different high-level optimization schemes). It will accordingly be understood that such modifications, alterations, and combinations are to be viewed as being within the ambit of the inventive concept.

What is claimed is:

1. A method comprising:

by a control circuit, while optimizing a radiation treatment plan for a particular patient:

outsourcing an optimization calculation to an external resource;

receiving from the external resource a resultant optimization calculation; and using the resultant optimization calculation during a current optimization cycle.

2. The method of claim 1, wherein the optimization calculation comprises an optimization high-level utility function calculation.

3. The method of claim 1, wherein the optimization calculation comprises an optimization cost function.

4. The method of claim 1, wherein the control circuit is configured to outsource the optimization calculation to the external resource once during each optimization loop.

5. The method of claim 1, wherein the control circuit cannot control a formatting of a function by which the external resource calculates the optimization calculation.

6. The method of claim 1, wherein the control circuit, while optimizing the radiation treatment plan for the particular patient, is further configured to:

determine at least one optimization variable value;

provide the at least one optimization variable value to the external resource when outsourcing the optimization calculation.

7. The method of claim 1, wherein the control circuit, while optimizing the radiation treatment plan for the particular patient, is further configured to:

determine at least two different optimization variable values;

provide the at least two different optimization variable values to the external resource when outsourcing the optimization calculation.

8. The method of claim 1, wherein the control circuit, while optimizing the radiation treatment plan for the particular patient, is further configured to:

determine at least three different optimization variable values;

provide the at least three different optimization variable values to the external resource when outsourcing the optimization calculation.

9. The method of claim 1, wherein the external resource comprises a third-party resource.

10. The method of claim 1, wherein the control circuit is further configured to:

receive an address for the external resource;

and wherein the control circuit is configured to outsource the optimization calculation to the external resource by using the address for the external resource.

11. An apparatus comprising:

a control circuit configured to, while optimizing a radiation treatment plan for a particular patient:

outsource an optimization calculation to an external resource; and receive from the external resource a resultant optimization calculation.

12. The apparatus of claim 11, wherein the optimization calculation comprises an optimization high-level utility function calculation.

13. The apparatus of claim 11, wherein the optimization calculation comprises an optimization cost function.

14. The apparatus of claim 11, wherein the control circuit is configured to outsource the optimization calculation to the external resource once during each optimization loop.

15. The apparatus of claim 11, wherein the control circuit cannot control a formatting of a function by which the external resource calculates the optimization calculation.

16. The apparatus of claim 11, wherein the control circuit, while optimizing the radiation treatment plan for the particular patient, is further configured to:

determine at least one optimization variable value;

provide the at least one optimization variable value to the external resource when outsourcing the optimization calculation.

17. The apparatus of claim 11, wherein the control circuit, while optimizing the radiation treatment plan for the particular patient, is further configured to:

determine at least two different optimization variable values;

provide the at least two different optimization variable values to the external resource when outsourcing the optimization calculation.

18. The apparatus of claim 11, wherein the control circuit, while optimizing the radiation treatment plan for the particular patient, is further configured to:

determine at least three different optimization variable values;

provide the at least three different optimization variable values to the external resource when outsourcing the optimization calculation.

19. The apparatus of claim 11, wherein the external resource comprises a third-party resource.

20. The apparatus of claim 11, wherein the control circuit is further configured to:

receive an address for the external resource;

and wherein the control circuit is configured to outsource the optimization calculation to the external resource by using the address for the external resource.

* * * * *